(12) United States Patent
Lee et al.

(10) Patent No.: US 11,957,443 B2
(45) Date of Patent: Apr. 16, 2024

(54) SYSTEM AND METHOD FOR ELECTRICAL IMPEDANCE TOMOGRAPHY OF AN OBJECT, AND AN IMPEDANCE MEASUREMENT UNIT

(71) Applicant: Stichting IMEC Nederland, AE Eindhoven (NL)

(72) Inventors: Seulki Lee, Eindhoven (NL); Mario Konijnenburg, Best (NL); Gijs Van Gestel, Beerse (BE); Nahm Il Koo, Eindhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 238 days.

(21) Appl. No.: 17/541,671

(22) Filed: Dec. 3, 2021

(65) Prior Publication Data

US 2022/0178980 A1 Jun. 9, 2022

(30) Foreign Application Priority Data

Dec. 4, 2020 (EP) .................................... 20211987

(51) Int. Cl.
*A61B 5/0536* (2021.01)
*G01R 17/02* (2006.01)
*G01R 27/26* (2006.01)

(52) U.S. Cl.
CPC ............ *A61B 5/0536* (2013.01); *G01R 17/02* (2013.01); *G01R 27/2605* (2013.01)

(58) Field of Classification Search
CPC ... A61B 5/0536; G01R 17/02; G01R 27/2605
See application file for complete search history.

(56) References Cited

U.S. PATENT DOCUMENTS 5,544,662 A    8/1996   Saulnier et al.
6,236,886 B1 *   5/2001   Cherepenin ............ A61B 5/418
                                                    600/547

(Continued)

FOREIGN PATENT DOCUMENTS

GB        2530355 A     3/2016

OTHER PUBLICATIONS

Tong et al., "A fully parallel multi-frequency EIT system with flexible electrode configuration: KHU Mark2", Physiological Measurement, vol. 32, No. 7, pp. 835-849, Jun. 2011.

(Continued)

*Primary Examiner* — Amy He
(74) *Attorney, Agent, or Firm* — MOSER TABOADA

(57) ABSTRACT

A system for electrical impedance tomography comprises: a plurality of electrodes; a plurality of impedance measurement units, each being associated with two or more electrodes, and wherein each impedance measurement unit comprises a current generator for generating a stimulation current between the electrodes and an amplifier for amplifying a measurement voltage between the electrodes; wherein the system is configured to perform a plurality of impedance measurements, wherein, for each impedance measurement, one impedance measurement unit is set in a stimulation mode for providing a stimulation current into the object, and wherein the impedance measurement unit being set in the stimulation mode is switched among the plurality of impedance measurement units, and wherein each impedance measurement unit is configured to be set in a calibration mode during at least one of the plurality of impedance measurements.

13 Claims, 7 Drawing Sheets

(56) References Cited

U.S. PATENT DOCUMENTS

| | | |
|---|---|---|
| 7,701,227 B2 * | 4/2010 | Saulnier ............... A61B 5/0536 |
| | | 324/601 |
| 2004/0158167 A1 | 8/2004 | Smith et al. |
| 2008/0001608 A1 | 1/2008 | Saulnier et al. |

OTHER PUBLICATIONS

Wi et al., "Multi-Frequency Electrical Impedance Tomography System With Automatic Self-Calibration for Long-Term Monitoring", IEEE Transactions on Biomedical Circuits and Systems, vol. 8, No. 1, pp. 119-128, Feb. 2014.
Jang et al., "A 2.79-mW 0.5%-THD CMOS Current Driver IC for Portable Electrical Impedance Tomography System", IEEE Asian Solid-State Circuits Conference, Seoul, Korea, Nov. 6-8, 2017, pp. 145-148.
Kim et al., "A 1.4-m Ω-Sensitivity 94-dB Dynamic-Range Electrical Impedance Tomography SoC and 48-Channel Hub-SoC for 3-D Lung Ventilation Monitoring System", IEEE Journal of Solid-State Circuits, vol. 52, No. 11, pp. 2829-2842, Nov. 2017.
Rapin et al., "Wearable Sensors for Frequency-Multiplexed EIT and Multilead ECG Data Acquisition", IEEE Transactions on Biomedical Engineering, vol. 66, No. 3, pp. 810-820, Mar. 2019.
Extended European Search Report in EP20211987.1 dated May 19, 2021.

* cited by examiner

SYSTEM AND METHOD FOR ELECTRICAL IMPEDANCE TOMOGRAPHY OF AN OBJECT, AND AN IMPEDANCE MEASUREMENT UNIT

TECHNICAL FIELD

The present inventive concept relates to electrical impedance tomography of an object. In particular, the present inventive concept relates to electrical impedance tomography using a plurality of impedance measurement units.

BACKGROUND

Electrical impedance tomography (EIT) allows determining an impedance map of an internal part of an object. EIT is of particular interest for medical imaging of an interior of a body, since EIT is non-invasive and uses no ionizing or heating radiation.

EIT measurements requires multiple electrodes. A spatial resolution of an image reconstructed based on EIT measurements is related to a number of electrodes used. If EIT measurements are controlled by a single integrated circuit, it may be difficult to add electrodes for adapting an EIT system to an increased need in resolution or image size.

Therefore, in order to improve versatility in defining the EIT system in dependence of needs of a particular measurement, it may be beneficial to enable several different impedance measurement units to be connected to each other, wherein each impedance measurement unit may be formed by a separate integrated circuit. Thus, the number of impedance measurement units to be used may be selected for respective EIT measurements to be made.

However, each impedance measurement unit may comprise a current generator and an amplifier for amplifying a measurement voltage. Since different impedance measurement units are used, there may be variations in characteristics e.g. of the current generator and the amplifier between different impedance measurement units. For this reason, it may be important to calibrate the impedance measurement units to avoid errors due to different characteristics of the impedance measurement units.

In Wi H. et al, "Multi-Frequency Electrical Impedance Tomography System With Automatic Self-Calibration for Long-Term Monitoring", IEEE Transactions on Biomedical Circuits and Systems, Vol. 8, No. 1, February 2014, pages 119-128, an EIT system using multiple impedance measurement modules is disclosed. It is disclosed that a calibration is made using a resistor phantom reducing calibration tasks of an operator. It is further discussed that signal-to-noise ratio and reciprocal error were satisfactory for some time after calibration, up to 1 week.

However, there may still be a need to improve robustness and accuracy of EIT measurements using a plurality of impedance measurement units.

SUMMARY

An objective of the present inventive concept is to enable robust electrical impedance tomography. It is a particular objective of the present inventive concept to enable electrical impedance tomography to be performed continuously while not being affected by varying conditions.

These and other objectives of the present inventive concept are at least partly met by the invention as defined in the independent claims. Preferred embodiments are set out in the dependent claims.

According to a first aspect, there is provided a system for electrical impedance tomography of an object, said system comprising: a plurality of electrodes configured to be attached to the object; a plurality of impedance measurement units, wherein each impedance measurement unit is associated with two or more electrodes of the plurality of electrodes, and wherein each impedance measurement unit comprises a current generator for generating a stimulation current between the electrodes associated with the impedance measurement unit and an amplifier for amplifying a measurement voltage between the electrodes associated with the impedance measurement unit; wherein the system is configured to perform a plurality of impedance measurements, wherein, for each impedance measurement, one impedance measurement unit among the plurality of impedance measurement units is set in a stimulation mode for providing a stimulation current into the object between the electrodes associated with the one impedance measurement unit, and wherein the impedance measurement unit being set in the stimulation mode is switched among the plurality of impedance measurement units between different measurements in the plurality of impedance measurements, and wherein each impedance measurement unit is configured to be set in a calibration mode during at least one of the plurality of impedance measurements for calibration of the impedance measurement unit during electrical impedance tomography measurements.

The system for electrical impedance tomography (EIT) uses a plurality of impedance measurement units. This implies that the system may allow to be adapted to a particular application, such that one or more impedance measurement units may be added or removed from the system to allow the system to support use of a number of electrodes as needed in the particular application. This allows the system to be versatile to be used in different applications.

Furthermore, each impedance measurement unit comprises a current generator and an amplifier and characteristics of the impedance measurement units may vary, e.g. due to variations in manufacturing of the impedance measurement units. Variations caused in manufacturing may be compensated for by calibrating the impedance measurement units before the system is used. According to the first aspect, the system also allows calibration to be performed to ensure that the system is continuously calibrated to provide reliable results. This may be particularly important in continuous use of the system to monitor EIT of an object. It is an insight of the inventive concept, that in continuous monitoring e.g. in a wearable, environmental variations (such as stray capacitance, temperature, humidity) frequently occur that may affect output of the current generator and amplification by the amplifier. Hence, if calibration were to be performed separately while the system is not in use, interruption in monitoring of EIT may be needed often. This would also be detrimental to use of the system by a user who is not acquainted with doing calibrations, e.g. a patient wearing the system for use during daily life, since the user may need to visit a person who can make the calibration as often as every day. Thus, thanks to the system allowing calibration to performed continuously and during use of the system, reliable EIT measurements may be provided over a long period of time and with no requirements on manual handling by a user or an operator.

In EIT measurements, a plurality of electrodes is used, and the electrodes being used for providing a stimulation current into the object are switched among the plurality of impedance measurements. This implies that the impedance measurement unit may anyway be switched between a stimulation mode and a measurement mode. According to the system of the first aspect, an additional mode, the calibration mode, is defined such that the impedance measurement units may also be set in the calibration mode during the EIT measurements. As multiple measurements are performed by each impedance measurement unit while switching which impedance measurement unit is set in the stimulation mode, setting the impedance measurement unit in the calibration mode once among the plurality of impedance measurements will not highly affect an amount of information that may be acquired by the impedance measurement unit. Furthermore, as will be described below, the impedance measurement unit may be set in the calibration mode, when the impedance measurement unit shares an electrode with the impedance measurement unit being set in the stimulation mode such that the impedance measurement unit in the calibration mode could not anyway be used in the measurement mode at that time. Thus, even when setting the impedance measurement units in calibration mode, no information that may be acquired by the impedance measurement units need be lost.

Each impedance measurement unit may be a separate, self-contained unit for providing signals to the electrodes associated with the impedance measurement unit and measuring signals from the electrodes. For instance, each impedance measurement unit may be arranged as a separate integrated circuit. Each impedance measurement unit may further comprise an interface e.g. for receiving control signals to the impedance measurement unit and for outputting measurement results. The impedance measurement units may be configured to communicate with each other and/or with a common additional unit.

Each impedance measurement unit may be associated with two or more electrodes of the plurality of electrodes. For instance, each impedance measurement unit may be associated with two electrodes, which implies that the impedance measurement unit may generate a stimulation current between the two electrodes and may amplify a measurement voltage between the same two electrodes. However, according to another embodiment, each impedance measurement unit may be associated with four electrodes, which implies that the impedance measurement unit may generate a stimulation current between a first pair of electrodes among the four electrodes and may amplify a measurement voltage between a second pair of electrodes among the four electrodes, wherein the first and the second pairs are different. According to yet another embodiment, each impedance measurement unit may be associated with three electrodes, such that one electrode is shared and used both in generating a stimulation current and for receiving a measurement voltage. Also, it should be realized that all impedance measurement units need not be associated with a same number of electrodes. Rather, some impedance measurement units may be associated with two electrodes while other impedance measurement units may be associated with four electrodes.

An impedance measurement may be performed by detecting and amplifying a measurement voltage between electrodes in an impedance measurement unit, while another impedance measurement unit is set in the stimulation mode for providing a stimulation current into the object. At a single point in time when one impedance measurement unit is set in the stimulation mode, a subset of impedance measurements may be performed by measurement voltages being detected by several impedance measurement units. It should further be realized that the plurality of impedance measurements is performed in a plurality of points in time for detecting a plurality of subsets of impedance measurements together forming the plurality of impedance measurements. The impedance measurement unit being set in the stimulation mode is switched among the plurality of impedance measurement units between different points in time for detecting the impedance measurements.

At a single point in time, a single impedance measurement unit may be set in the stimulation mode for providing a stimulation current into the object. The impedance measurement units detecting a measurement voltage at the single point in time may thus all detect a measurement voltage between the respective electrodes associated with the impedance measurement unit as a response to the same stimulation current between the electrodes associated with the impedance measurement unit being set in the stimulation mode.

Switching of the impedance measurement units being set in the stimulation mode may be performed by sequentially sweeping the impedance measurement units until all impedance measurement units have been set in the stimulation mode. When a full sweep has been performed, an entire set of the plurality of impedance measurements may be acquired allowing an EIT image to be formed. However, it should be realized that all impedance measurement unit need not necessarily be set in the stimulation mode during the plurality of impedance measurements. For instance, if the electrodes are arranged on a line, the impedance measurement unit(s) associated with outermost electrodes on the line need not be set in the stimulation mode.

It should also be realized that switching of the impedance measurement units being set in the stimulation mode during acquisition of the plurality of impedance measurements may be performed in many different manners. For instance, an order in which the impedance measurement units are set in the stimulation mode may be varied in many different ways. Also, the number of times each impedance measurement unit is set in the stimulation mode during a plurality of impedance measurements for acquisition of measurements for forming an EIT image may vary between different impedance measurement units, such that e.g. some impedance measurement units may never be set in the stimulation mode, some impedance measurement units may be set once in the stimulation mode and some impedance measurement units may be set twice in the stimulation mode. This may imply that some parts of the object may be imaged with better accuracy and/or resolution. However, it may be preferred that each impedance measurement unit is set once in the stimulation mode during acquisition of the plurality of impedance measurements.

A system may be set up to always use same settings for switching the impedance measurement units being set in the stimulation mode. However, different systems may use different settings according to alternatives discussed above. Further, it should be realized that settings may also be changed for a particular system, e.g. to adapt the system to an object for which EIT is performed.

According to an embodiment, each impedance measurement unit is configured to be set in the stimulation mode during at least one impedance measurement of the plurality of impedance measurements.

Hence, each measurement unit may be set in the stimulation mode during at least one point in time for acquisition of impedance measurements. This implies that all measurement units are set in the stimulation mode at some point in time to allow making impedance measurements in relation to all different electrode pairs in the system being used for providing the stimulation current. Hence, an EIT image may be formed with a maximum spatial extension available using the plurality of impedance measurement units.

According to an embodiment, in the calibration mode, the impedance measurement unit is configured to calibrate a current generated by the current generator of the impedance measurement unit.

This implies that the current generated by the current generator in the impedance measurement unit may be known after the impedance measurement unit has been set in the calibration mode. An error in the current generated by the current generator may otherwise result in an error in forming of an EIT image, such that accuracy of the EIT image may be affected.

Variations in current generated by the current generator may be caused by environmental factors in which the system is used, such as stray capacitance, temperature, and humidity. In particular, when the system is used as a wearable to be worn over a long period of time by a user, variations in environmental factors may frequently occur, such as differences in temperature and humidity between the user being indoors or outdoors.

It should be realized that calibration of the current generated by the current generator may comprise controlling the current generator to ensure that a current with a desired amplitude is generated, e.g. by adjusting an output impedance of the current generator. However, according to an alternative, calibration of the current generated by the current generator may comprise measuring an amplitude of the current generated by the current generator and storing the measured amplitude so as to enable the stored measured amplitude to be used as compensation when forming an EIT image. According to yet another alternative, the calibration may ensure that the current generator generates a current having an amplitude within a desired range and measuring and storing the amplitude to which the current generator is set.

According to an embodiment, the impedance measurement unit comprises unity gain buffers configured to be connected to nodes on opposite sides of the current generator in calibration measurements for calibrating the current generated by the current generator.

An amplitude of the current generated by the current generator may be determined by measuring a voltage between the nodes on opposite sides of the current generator while the current generator generates a current through a resistor with a well-known resistance. Thanks to connecting each node to a unity gain buffer, connection of the nodes to an analog-to-digital converter (ADC) for obtaining a digital measurement of the voltage between the nodes is facilitated.

The ADC may be re-used in reading a voltage for calibration of the current generator and for reading an amplified measurement voltage. Thus, the amplifier may be disconnected from the ADC in the calibration mode, when calibrating the current generator, and instead be connected to unity gain buffers.

According to an embodiment, in the calibration mode, the impedance measurement unit is configured to calibrate a gain of the amplifier.

This implies that the gain provided by the amplifier in the impedance measurement unit may be known after the impedance measurement unit has been set in the calibration mode. An error in the gain provided by the amplifier may otherwise result in an error in forming of an EIT image, such that accuracy of the EIT image may be affected.

As for the current generated by the current generator, variations in gain provided by the amplifier may be caused by environmental factors in which the system is used, such as stray capacitance, temperature, and humidity. In particular, when the system is used as a wearable to be worn over a long period of time by a user, variations in environmental factors may frequently occur, such as differences in temperature and humidity between the user being indoors or outdoors.

It should be realized that calibration of the gain provided by the amplifier may comprise adjusting the amplifier to ensure that a desired gain is provided. However, according to an alternative, calibration of the gain provided by the amplifier may comprise measuring a gain of the amplifier and storing the measured gain so as to enable the stored measured gain to be used as compensation when forming an EIT image. According to yet another alternative, the calibration may ensure that the amplifier provides a gain within a desired range and measuring and storing the gain to which the amplifier is set.

According to an embodiment, each impedance measurement unit comprises a reference resistor, which is configured to be connected to the current generator in the calibration mode for calibration of the impedance measurement unit.

Thus, a reference resistor having a known reference resistance may be used for calibration. As the reference resistor is provided in the impedance measurement unit, calibration measurements may be performed completely within the impedance measurement unit.

The reference resistor should be configured to provide a stable reference resistance, which does not vary within any environmental variations (such as stray capacitance, temperature, humidity) to which the system is expected to be subject. Further, the reference resistance may be configured to provide the stable reference resistance over a long period of time, so as to avoid a need of externally calibrating the reference resistor.

The reference resistor may be used in calibrating the current generated by the current generator, by the current generated by the current generator being driven through the reference resistor.

The reference resistor may also be used in calibrating the gain of the amplifier. Thus, when calibrating the gain of the amplifier, the current generated by the current generator may be driven through the reference resistor, while the amplifier may be connected to nodes on opposite sides of the current generator. Thus, based on the current generator being calibrated and the resistance of the reference resistor being known, the input voltage to the amplifier is known such that the output voltage from the amplifier may be compared to the known input voltage for determining the gain.

According to an embodiment, each impedance measurement unit is associated with two neighboring electrodes in the plurality of electrodes, and wherein an electrode is shared by two neighboring impedance measurement units in the plurality of impedance measurement units.

Thanks to an electrode being shared by two neighboring impedance measurement units, the impedance may be measured between all pairs of neighboring electrodes in the two neighboring impedance measurement units. Further, if all pairs of neighboring impedance measurement units are configured to share an electrode, the impedance measurement units in the system may measure impedances between each pair of neighboring electrodes in the system. This implies that there will not be any two neighboring electrodes between which an impedance is not measured, which further implies that an EIT image may be formed throughout an entire space of the object associated with the plurality of electrodes. Hence, no white spaces lacking any information in the EIT image may be present.

In particular, if all impedance measurement units are associated with two electrodes, both electrodes of an impedance measurement unit may be shared, the electrodes being shared with different impedance measurement units on opposite sides. It should be realized that all electrodes are not necessarily shared by two impedance measurement units. For instance, if the electrodes are arranged on a line, the electrodes at respective ends of the line will not be shared by two impedance measurement units.

According to an embodiment, for a subset of impedance measurements in the plurality of impedance measurements, the subset being acquired at a single point in time, two impedance measurement units being arranged on opposite sides of and neighboring to the one impedance measurement unit being set in the stimulation mode are configured to be set in the calibration mode.

At a point in time when an impedance measurement unit is set in the stimulation mode, the electrodes of the impedance measurement unit being in the stimulation mode are used for providing a stimulation current into the object. Since these electrodes are shared with the impedance measurement units on opposite sides of the impedance measurement unit being in the stimulation mode, these two impedance measurement units each being associated with an electrode that is being used for stimulation may anyway not be suitable for being used in measuring an impedance. Thus, as the impedance measurement units may not be suitably used for measuring an impedance, the point in time may be utilized instead for calibrating the impedance measurement units.

Hence, the calibration of impedance measurement units may be performed at a point in time when the impedance measurement unit is anyway not available for performing an impedance measurement.

While it is possible to perform calibration of two neighboring impedance measurement units while an impedance measurement unit is set in the calibration mode, it should be realized that it may not be necessary, at least at each point in time to perform calibration of two impedance measurement units. Rather, each impedance measurement unit may be calibrated only once during sweeping of the impedance measurement units being set in the stimulation mode. However, in a set-up where the electrodes are arranged on a line, at least at one point in time, two impedance measurement units neighboring to the impedance measurement unit in the stimulation mode may need to be set in the calibration mode.

As used herein, the term "at a single point in time" should not be construed as necessarily being exactly simultaneous. Thus, the impedance measurement units used for acquiring a subset of impedance measurements need not perform the impedance measurements exactly simultaneously. However, the impedance measurements may be performed during a common period of time wherein stimulation is provided from a single impedance measurement unit being set in the stimulation mode. Thus, a duration of the point in time may correspond to a duration of the stimulation current being provided from the impedance measurement unit being in the stimulation mode.

According to an embodiment, for a subset of impedance measurements in the plurality of impedance measurements, the subset being acquired at a single point in time, each impedance measurement unit not being in the stimulation mode or the calibration mode is set in a measurement mode for measuring a voltage between the electrodes associated with the impedance measurement unit.

Thus, at each single point in time, several impedance measurements may be acquired by the impedance measurement units not being in the calibration mode or in the stimulation mode.

For instance, the two impedance measurement units on opposite sides of the measurement unit being in the stimulation mode may be set in the calibration mode. This implies that if the system comprises N channels (impedance measurement units), N−3 channels may be set in the measurement mode at each such point in time. However, if the electrodes are arranged on a line, the impedance measurement units at the ends of the line will only have one neighbor, and when these impedance measurement units are set in the stimulation mode, N−2 channels may be set in the measurement mode.

Further, as discussed above, an impedance measurement unit need not necessarily be set in the calibration mode at both points in time when the neighboring measurement units are set in the stimulation mode. Rather, the impedance measurement unit may be set in the calibration mode at a first point in time during which a first neighboring measurement unit is set in the stimulation mode and may be set in an inactive mode at a second point in time during which a second neighboring measurement unit is set in the stimulation mode.

According to an embodiment, the system is configured to set one of the impedance measurement units in the plurality of impedance measurement units as a master impedance measurement units and remaining impedance measurement units as slave impedance measurement units, wherein the master impedance measurement unit is configured to communicate with the slave impedance measurement units for controlling operation of the slave impedance measurement units.

This implies that an overall control of the impedance measurement units may be provided. The impedance measurement units may all be identical, and a selection of a master impedance measurement unit may be arbitrarily made upon setting up of the system. This implies that manufacturing may be facilitated, as there need not be different manufacturing steps for manufacturing master impedance measurement units and slave impedance measurement units.

The master impedance measurement unit may be connected to each slave impedance measurement unit for communicating with each of the slave impedance measurement units directly. However, according to an embodiment, the impedance measurement units may be connected in series, such that signals from the master impedance measurement unit may be forwarded by slave impedance measurement units for reaching a destination among the slave impedance measurement units.

The master impedance measurement unit may control which mode to be used for each impedance measurement unit at a given point in time. It should be realized that the master impedance measurement unit may control the mode of each impedance measurement unit by providing control signals to the impedance measurement units identifying the mode to be used. However, according to an alternative, the master impedance measurement unit need only provide a control signal indicating that a next mode is to be used. Each slave impedance measurement unit may store a sequence of modes to be used, such that when a next mode control signal is used, the slave impedance measurement unit may select the next mode indicated by the stored sequence. This implies that the master impedance measurement unit may send a simple control signal which is the same control signal for all slave impedance measurement units and may be used for synchronizing switching of modes.

The master impedance measurement unit may also control a frequency to be used by the stimulation current provided by the impedance measurement unit in the stimulation mode. This may be used when a multi-frequency EIT image is to be formed.

According to an embodiment, the master impedance measurement unit is configured to generate a master clock signal and to transmit the clock signal to the slave impedance measurement units for synchronizing clocks of the plurality of impedance measurement units.

This implies that clocks of all the impedance measurement units are synchronized to avoid any errors in measurements due to differences in clock signals.

This implies that errors due to clock variations may be avoided. For instance, impedance measurements may involve modulation for forming I- and Q-channel signals. Clock variations may affect the impedance modulation and cause errors in an EIT image being formed. Hence, by providing the clock signal from the master impedance measurement unit, such errors may be avoided or at least reduced.

According to an embodiment, the system comprises at least one safety circuit in connections between the impedance measurement unit and the electrodes, wherein the at least one safety circuit is configured to prevent a transient current spike to cause harm to the object.

Thus, the safety circuit may ensure that use of the system for performing EIT measurements will not present a danger to harming or hurting the object. This is particularly important when EIT measurements are to be performed on a human being.

It should be realized that many different types of safety circuits are available, using an active or passive safety circuit.

The safety circuit may be part of the impedance measurement unit and may thus be arranged in an interface between the impedance measurement unit and the electrodes. However, the safety circuit may alternatively be separate to the impedance measurement unit and safety circuits may be arranged in between each electrode and impedance measurement units associated with the electrode.

According to an embodiment, each impedance measurement unit comprises a safety circuit, comprising DC blocking capacitors in connections between the current generator and the electrodes associated with the impedance measurement unit and resistors in connections between the amplifier and the electrodes associated with the impedance measurement unit.

This implies that transient current spikes may be prevented from reaching or at least reduced before reaching the object. This is a simple circuitry while providing safety to the object on which EIT measurements are performed.

It should be realized that the use of multiple impedance measurement units ensures that each electrode may be statically connected to a current generator and an amplifier. Thus, compared to a system having a single or a few current generator(s) and amplifier(s) with a multiplexing set-up for switching connections to the electrodes, the use of multiple impedance measurement units allows placing capacitors between current generators and electrodes and resistors between amplifiers and electrodes for providing safety to the object. Hence, in the system using multiple impedance measurement unit, the safety circuit may be provided in a simple manner.

According to an embodiment, each impedance measurement unit comprises an output for communicating impedance measurement results from the impedance measurement units, wherein the plurality of impedance measurement units is configured to share a wire for communication.

This implies that communication of impedance measurement results may be provided on one or a few wires. Hence, complexity of the system is reduced.

A communication protocol may be used by the impedance measurement units on the shared wire in order to allow sharing of the wire for communication. For instance, an impedance measurement unit may receive a control signal to indicate that the impedance measurement unit may output information on the shared wire. Thus, traffic on the shared wire may be controlled for ensuring that the impedance measurement units sharing a wire does not cause errors in transmission of information.

According to a second aspect, there is provided an electrical impedance tomography apparatus comprising the system according to the first aspect, wherein the apparatus is configured to be worn by a subject and wherein the apparatus is configured to continuously monitor bioimpedance of the subject while the apparatus is worn.

Effects and features of this second aspect are largely analogous to those described above in connection with the first aspect. Embodiments mentioned in relation to the first aspect are largely compatible with the second aspect.

EIT imaging is of particular interest in medical imaging applications, because EIT measurements are non-invasive and uses no ionizing or heating radiation. Thus, the apparatus may be configured to measure bioimpedance of a body of the subject and use the measured bioimpedance for imaging internal parts of the body. EIT imaging may for instance be used in monitoring of breathing, which may be useful e.g. for controlling lung ventilation therapy, or in monitoring an intracranial pressure in a skull.

Furthermore, the system of the first aspect may advantageously be used for continuous monitoring of the subject and, in particular, in an apparatus that is configured to be worn by the subject. Thanks to the system allowing impedance measurement units to be calibrated efficiently during use, the system may stay calibrated for a long time. Also, when the apparatus is worn by the subject, the apparatus may be particularly likely to be exposed to environmental variations, such as variations that may be due to the subject moving between different conditions, e.g. indoor and outdoor conditions. This facilitates use of the system in the EIT apparatus that is configured to continuously monitor bioimpedance of the subject while the apparatus is worn by the subject.

However, it should be realized that the system according to the first aspect may be implemented in many different applications and need not necessarily be used for monitoring a human subject. Rather, the system may be configured to perform EIT measurements on an object in an industrial application. Thus, the object may be a building or a vessel in which a process takes place.

According to an embodiment, the system may be used to monitor moisture within a building, which may be useful for determining non-invasively if the building is damaged or affected by moisture.

According to an embodiment, the system may be used to monitor a process, e.g. a chemical process, which occurs within a vessel. Conditions within the vessel may be hazardous which may imply that it may be difficult to obtain measurements from within the vessel.

According to a third aspect, there is provided an impedance measurement unit configured to be used in a system for electrical impedance tomography according to the first aspect.

Effects and features of this third aspect are largely analogous to those described above in connection with the first and second aspects. Embodiments mentioned in relation to the first and second aspects are largely compatible with the third aspect.

The impedance measurement unit may be adapted for use in a system according to the first aspect. Impedance measurement units may be separately sold, and a user may thus acquire impedance measurement units and assemble the impedance measurement units into a system according to the first aspect. This implies that impedance measurement units may also be added to the system when needed, such that the user need not initially set up the system based on possible future needs of size of the system (numbers of electrodes and impedance measurement units).

According to a fourth aspect, there is provided an impedance measurement unit configured to be used in a system for electrical impedance tomography, wherein the impedance measurement unit comprises: a first and a second connection interface for connecting the impedance measurement unit to a first and a second electrode; a current generator for generating a stimulation current for output through the first and the second connection interface for providing a current between the first and the second electrode; an amplifier configured to receive input from the first and the second connection interface of a measurement voltage across the first and the second electrode, said amplifier being configured to amplify the measurement voltage; and a control input interface for receiving a control signal for repeatedly shifting a mode of the impedance measurement unit between a stimulation mode, wherein the current generator is configured to generate the stimulation current, a measurement mode, wherein the amplifier is configured to receive the measurement voltage, and a calibration mode, wherein the current generator and the amplifier of the impedance measurement unit is calibrated.

Effects and features of this fourth aspect are largely analogous to those described above in connection with the first, second, and third aspects. Embodiments mentioned in relation to the first, second, and third aspects are largely compatible with the fourth aspect.

The impedance measurement unit may be adapted for use in a system according to the first aspect. Thanks to the impedance measurement unit being configured to be set in a stimulation mode, a measurement mode and a calibration mode based on receiving a control signal, the impedance measurement unit facilitates calibration to be performed while impedance measurements are performed by other impedance measurement units in a system.

Impedance measurement units may be separately sold, and a user may thus acquire impedance measurement units and assemble the impedance measurement units into a system according to the first aspect. This implies that impedance measurement units may also be added to the system when needed, such that the user need not initially set up the system based on possible future needs of size of the system (numbers of electrodes and impedance measurement units).

According to an embodiment, the impedance measurement unit further comprises a sequencer unit configured for storing a sequence of modes to be used by the impedance measurement unit, wherein the control signal is configured to initiate shifting to a next mode indicated by the stored sequence of modes in the sequencer unit.

The sequencer unit may thus hold information of the sequence of modes to be used by the impedance measurement unit. On set-up of a system, the sequencer unit of each impedance measurement unit may be provided with a respective sequence such that each impedance measurement unit carries information of the sequence of modes to be used. In this manner, the impedance measurement unit is adapted to shift between desired modes by receiving a simple control signal which may be identical for all impedance measurement units. Thus, during operation, the impedance measurement unit may itself, through the sequencer unit, keep track of which mode to use, wherein the mode used fits with the modes used by the other impedance measurement units of the system.

According to a fifth aspect, there is provided a method for electrical impedance tomography of an object by a system comprising a plurality of electrodes and a plurality of impedance measurement units wherein each impedance measurement unit is associated with two electrodes of the plurality of electrodes, said method comprising for performing an impedance measurement: setting one impedance measurement unit into a stimulation mode for providing a stimulation current into the object between the electrodes associated with the one impedance measurement unit; setting impedance measurement units on opposite sides of and neighboring to the one impedance measurement unit being set in the stimulation mode into a calibration mode for calibration of the impedance measurement unit; and setting impedance measurement units not being in the stimulation mode or the calibration mode into a measurement mode for measuring a voltage between the electrodes associated with the impedance measurement unit.

Effects and features of this fifth aspect are largely analogous to those described above in connection with the first, second, third, and fourth aspects. Embodiments mentioned in relation to the first, second, third, and fourth aspects are largely compatible with the fifth aspect.

The method may ensure that the impedance measurement units are calibrated to allow accurate EIT measurements to be performed over a long period of time without requiring EIT measurements to be interrupted for calibration purposes.

The impedance measurement units are set in the stimulation mode, calibration mode and measurement mode, respectively, at a simultaneous point in time such that measurements are performed while stimulation is provided from one impedance measurement unit and while calibrations are performed of the impedance measurement units on opposite sides of and neighboring to the one impedance measurement unit in the stimulation mode.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Electrical impedance tomography (EIT) provides non-invasive imaging of an interior part of an object. In EIT measurements, electrodes are arranged on a surface of the object, such as on skin of a human being, a small alternating stimulation current is applied between two electrodes and resulting voltages are measured between other electrodes. A process of applying stimulation currents and measuring resulting voltages may then be repeated for numerous different electrode configurations. All such EIT measurements may be used for forming an EIT image based on image reconstruction, wherein the EIT image may represent structures extending into the interior of the object.

EIT may be performed using a single frequency of the stimulation current. However, in some applications, multiple frequencies are used. When using multiple frequencies, the multiple frequencies may be used for every electrode configuration used in acquiring measurements.

Absolute EIT may be performed in order to image non-homogeneous structures in the object, such as to image different biological tissues in a body. Difference EIT may be performed in order to determine changes over time in the object.

Figure 1:
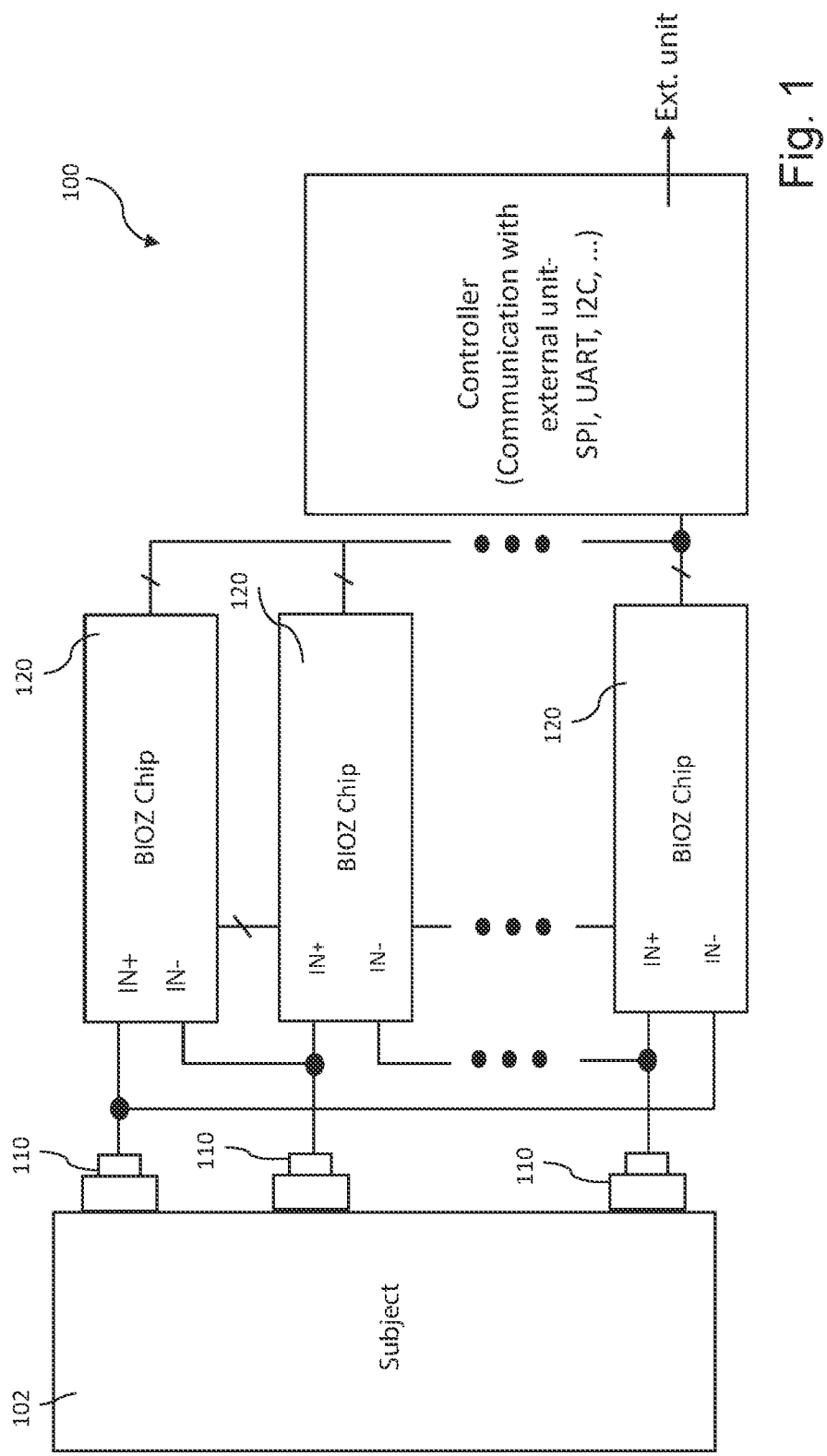
FIG. 1 is a schematic view of a system according to an embodiment.

Referring now to FIG. 1, a system 100 for performing EIT measurements on an object 102 will be described. The object 102 may be a human being, hereinafter referred to as a subject 102, such that the system 100 may be used for EIT imaging in a medical application based on measuring bio-impedance of the subject 102. Although the system 100 will be mainly discussed below in the context of a medical application, it should be realized that the system 100 may alternatively be used in other applications, such as for monitoring or measuring moisture of a building or for monitoring a process, e.g. a chemical process, which occurs within a vessel.

The system 100 may comprise a plurality of electrodes 110. The electrodes 110 are configured to be attached to the subject 102, e.g. by attachment to skin of the subject 102.

The plurality of electrodes 110 may be arranged in an array, wherein the electrodes 110 are arranged with equal spacings. The plurality of electrodes 110 may thus be configured for being arranged spatially distributed over a surface area, e.g. skin of the subject 102, related to a portion of the subject 102 for which an EIT image is desired.

The system 100 may further comprise a plurality of impedance measurement units 120. Each impedance measurement unit 120 may be associated with two or more electrodes 110 of the plurality of electrodes 110.

Figure 2:
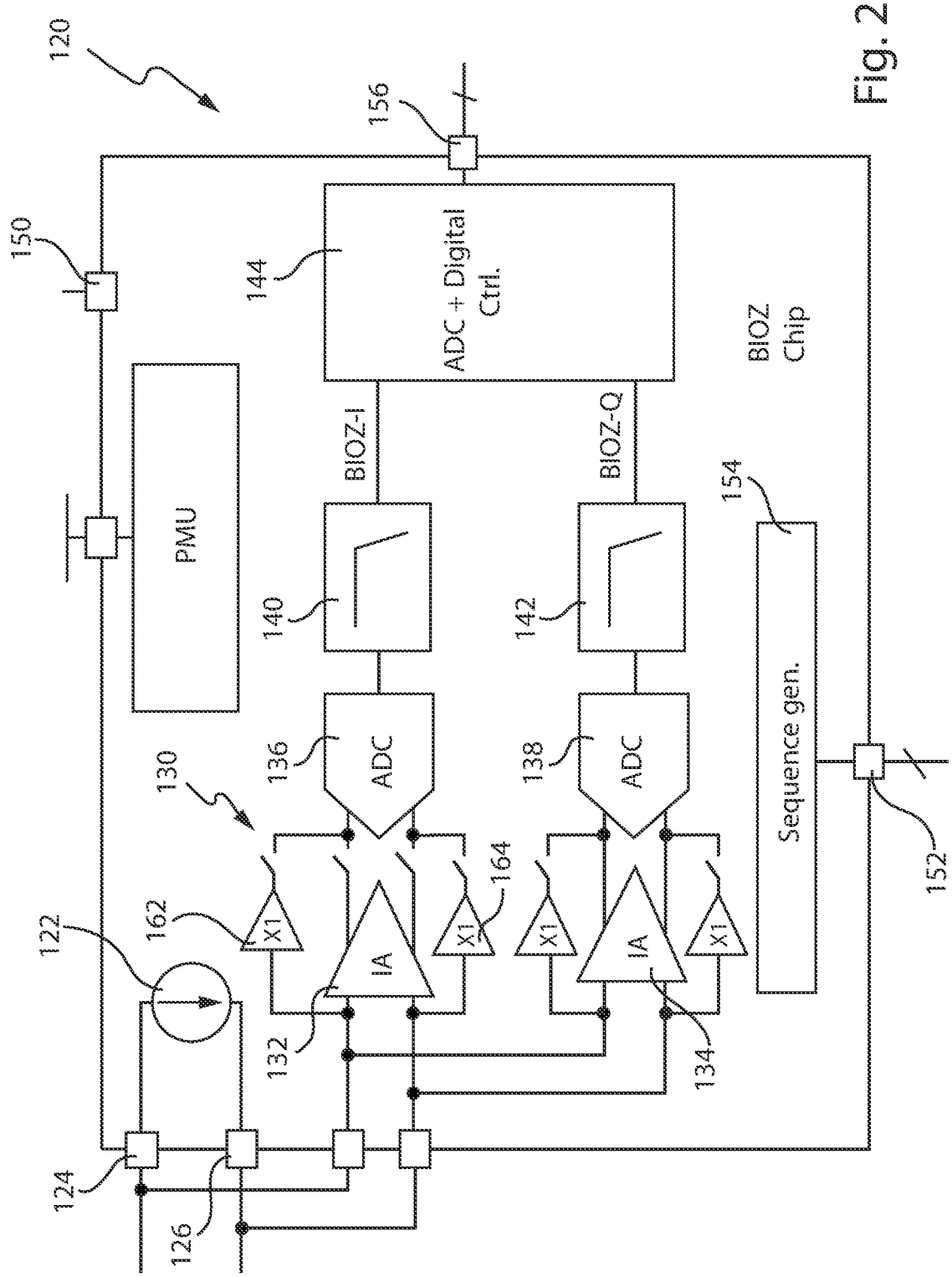
FIG. 2 is a schematic view of an impedance measurement unit of the system according to an embodiment.

Referring now to FIG. 2, each impedance measurement unit 120 may be dedicated for use with the electrodes 110 associated with the impedance measurement unit 120. Each impedance measurement unit 120 may comprise a current generator 122 for generating a stimulation current. The current generator 122 may be connected to two nodes 124, 126 on opposite sides of the current generator 122. The nodes 124, 126 may further form first and second connection interfaces, such as a plug and socket arrangement, for allowing the impedance measurement units to be connected to electrodes 110, such that the current generator 122 may be connected via the nodes 124, 126 to two electrodes 110 for generating a stimulation current between the electrodes 110. The generated stimulation current may thus propagate through the subject 102 causing voltage potentials between different parts of the subject 102.

Each impedance measurement unit 120 may further be configured to measure a voltage between electrodes 110 associated with the impedance measurement unit 120. The voltage may be measured between the same electrodes 110 used for providing a stimulation current into the subject 102. However, according to an alternative, two other electrodes 110 are used for measuring a voltage such that the impedance measurement unit 110 may be associated with four electrodes 110. According to yet another alternative, one electrode 110 is shared for providing the stimulation current and for measuring a voltage, such that the impedance measurement unit 110 may be associated with three electrodes.

In the embodiment shown in FIG. 2, the impedance measurement unit 120 is associated with two electrodes 110, such that the nodes 124, 126 are shared by the current generator 122 for providing a stimulation current to the electrodes 110 and a measurement circuit 130 for measuring a voltage across the electrodes 110.

The use of a plurality of impedance measurement units 120 have several advantages over a system based on a single unit, wherein a current generator and measurement circuit may be shared by all electrodes. In such a single-unit system, a multiplexer may be used for allowing selection of which electrodes are to be connected to the current generator and the measurement circuit. Compared to the single-unit system, the system 100 using a plurality of impedance measurement units 120 need not have any long cables for connecting the impedance measurement units 120 to the electrodes 110. This implies that parasitic capacitances and resistances due to long cables may be avoided and motion artefacts due to variations of parasitic capacitances and resistances by motion may avoided or at least reduced. For instance, the impedance measurement unit 120 may be configured to be arranged in close vicinity to the electrodes 110 associated with the impedance measurement unit 120. Further, the impedance measurement unit 120 may measure voltages and form digital representations of the measured voltages before transmitting results to an external unit. This also implies that the system 100 may be robust to parasitic capacitances and resistances in transmission of results.

According to an embodiment, the impedance measurement unit 120 may comprise a motion artefact sensor, such as a motion sensor and/or an electrode-tissue impedance sensor, for sensing movements that may affect measurements. The motion artefact sensor may thus provide information for motion artefact reduction or compensation per electrode 110.

Compared to the single-unit system, the system 100 using a plurality of impedance measurement units 120 may further be versatile and adjusted to a particular application in which the system 100 is to be used. Thus, the number of impedance measurement units 120 may be selected in dependence of current needs and may be adapted in different applications. Hence, the system 100 need not be designed during manufacturing for a maximum number of channels (electrodes 110) that are to be used. Rather, impedance measurement units 120 may be added, when needed.

Also, compared to the single-unit system, the system 100 using a plurality of impedance measurement units 120 may be more efficient in acquiring multiple voltage measurements. Since voltage measurements may be simultaneously performed by several impedance measurement units 120, instead of sequentially connecting electrodes to a measurement circuit via a multiplexer, speed of acquiring measurements for EIT may be increased substantially, especially when a large number of electrodes 110 are used. Thus, a frame rate of acquiring information for forming EIT images may be substantially increased.

The plurality of electrodes 110 may be mounted in an array configuration. Thus, the arrangement of the electrodes 110 in relation to each other may be well-defined in the array configuration, e.g. by the electrodes 110 being mounted on a carrier defining positions of the electrodes 110.

The carrier may be easily attached to the subject 102, such that arrangement of the system 100 in relation to the subject 102 may be facilitated. Also, the carrier may define positions of the electrodes 110 that are adapted for a particular application of EIT such that the mounting of the electrodes 110 on the carrier may provide a set-up for performing impedance measurements that is suited for the particular application. This implies that the arrangement of the carrier on the subject 102 may not need to be performed by a trained person.

However, as discussed above, the system 100 may be configured for allowing impedance measurement units 120 to be removed from or added to the system 100 based on adapting the system 100 to a particular application at hand. Thus, the system 100 may be versatile in being able to be adapted to include only relevant number of impedance measurement units 120 that are needed for the particular application. This enables the same system 100 to be adapted to be suited for relatively simple EIT applications and also for complex EIT applications.

Further, in order to have a system 100 that may be dynamically adapted based on the application in which it is to be used, the array of electrodes 110 may need to be freely changed to change the number of electrodes 110 and also interrelations between electrodes 110. In this respect, the arrangement of electrodes 110 in an array may only be defined when the electrodes 110 are attached to the subject 102.

As illustrated in FIG. 2, the measurement circuit 130 may comprise two channels for acquiring an in-phase component (I channel) and a quadrature component (Q channel) of the voltage across nodes 124, 126. In each channel, input related to each of the electrodes 110 connected to the respective nodes 124, 126 may be connected to inputs of an amplifier 132, 134. The amplifiers 132, 134 may thus be differential amplifiers for amplifying the difference between the input voltages associated with the two electrodes 110. According to an embodiment, the amplifiers 132, 134 may be instrumentation amplifiers.

In each channel, the output from the amplifier 132, 134 may further be provided to an analog-to-digital converter (ADC), 136, 138 for forming a digital representation of the amplified voltage difference. The digital output from the ADC 136, 138 may then be provided to a low-pass filter 140, 142, which may be useful in removing high-frequency noise. Finally, output from the low-pass filters 140, 142 may be provided to a control unit 144, wherein an I channel, and a Q channel output may be combined for forming a voltage measurement that represents impedance between the electrodes 110 associated with the impedance measurement unit 120.

Although described above based on dividing a measurement voltage into an I channel and a Q channel, it should be realized that the measurement voltage may be processed in other ways, such as using only a single channel with a single amplifier.

Each impedance measurement unit 120 may be set in a plurality of different modes of operation, wherein different functionalities of the impedance measurement unit 120 are activated. Each impedance measurement unit 120 may be set in a stimulation mode, wherein the current generator 120 is active for generating a stimulation current between electrodes 110 associated with the impedance measurement unit 120. Each impedance measurement unit 120 may further be set in a measurement mode, wherein the measurement circuit 130 is active for measuring a voltage between the electrodes 110 associated with the impedance measurement unit 120. Each impedance measurement unit 120 may further be set in a calibration mode for calibrating the current generator 122 and the measurement circuit 130.

When acquiring impedance measurements for EIT imaging, the impedance measurement units 120 are sequentially set in the stimulation mode. During each point in time when a particular impedance measurement unit 120 is set in the stimulation mode, a subset of impedance measurements may be acquired by impedance measurement units 120 not being in the stimulation mode may be set in the measurement mode for performing voltage measurements. Hence, at each point in time, a number of measurements are obtained. Further, since the impedance measurement units 120 may all be set in the stimulation mode in sequence, a number of subsets of impedance measurements may be acquired.

The impedance measurements may be performed for a single frequency being used by the current generators 122 of the impedance measurement units 120. Alternatively, the impedance measurements may be performed for multiple frequencies. In such case, different frequencies may be provided in sequence while a particular impedance measurement unit 120 is set in the stimulation mode. Alternatively, a single frequency is used while sequentially setting each impedance measurement unit 120 in the stimulation mode and then the frequency is changed and the impedance measurement units 120 are again sequentially set in the stimulation mode. This is repeated until impedance measurements have been acquired for all frequencies.

The frequencies used may differ substantially between different applications for EIT imaging. For instance, in brain imaging applications, single or multiple frequencies below 100 Hz may be used, whereas in other medical applications single or multiple frequencies in a range of 10-100 kHz may be used. In yet other applications, even higher frequencies may be used, such as frequencies up to 50 MHz.

An impedance measurement may be a measured voltage representing the resulting voltage across two electrodes 110 based on the stimulation current provided between two other electrodes. The measured voltage represents an impedance between the two electrodes 110 across which a voltage is measured. Although an actual impedance is a voltage divided by a current, the impedance measurement units 120 may output merely the measured voltage based on a known stimulation current. For instance, it should be noted that the measured voltage divided by the stimulation current may not directly represent the impedance between the two electrodes 110 because the current may be provided through a portion of the subject 102 relatively far away from the electrodes 110 used in a measurement, such that in such case, the measured voltage is relatively small. However, all the measured voltages may be used for forming an impedance map of the subject 102.

The results of all impedance measurements may be communicated to a processing unit. The processing unit may be part of the system 100 or may be external to the system 100. The processing unit may comprise algorithms for forming an EIT image based on the numerous impedance measurements. The processing unit may be part of one of the impedance measurement units 120 or may be arranged in a separate control unit of the system 100, which communicates with the impedance measurement units 120.

The processing unit may be implemented as a general-purpose processing unit, such as a central processing unit (CPU), which may execute the instructions of one or more computer programs in order to implement functionality of the processing unit.

The processing unit may alternatively be implemented as firmware arranged e.g. in an embedded system, or as a specifically designed processing unit, such as an Application-Specific Integrated Circuit (ASIC) or a Field-Programmable Gate Array (FPGA), which may be configured to implement functionality of the processing unit.

The reconstruction of an EIT image may require extensive processing power, and the processing unit may hence be suitably provided in an external unit. The system 100 may thus be configured to communicate with the external unit for transferring impedance measurements to the processing unit.

Each impedance measurement unit 120 may comprise a clock 150, which controls operation of the impedance measurement unit 120. Since the impedance measurement units 120 are separate from each other, each need its own clock 150 for controlling operations. However, there is a risk that clocks 150 of different impedance measurement units 120 will not stay synchronized for various reasons, such as clock jitter or different settling times of phase locked loops of the clocks 150. Further, if the clocks 150 are not synchronized, errors in impedance measurements may occur which may affect the EIT image being formed.

Therefore, the clocks 150 may advantageously be regularly synchronized in order to ensure that the clocks 150 stay synchronized. In this respect, one impedance measurement unit 120 may be set as a master impedance measurement unit which provides control over the remaining impedance measurement units 120 which form slave impedance measurement units.

The master impedance measurement unit may thus communicate with all the slave impedance measurement units for controlling operation of all the impedance measurement units 120 and ensure that the impedance measurement units 120 operate well together.

It should be realized that the control of operation of the impedance measurement units 120 may alternatively be provided by a separate control unit, which need not be part of any of the impedance measurement units 120.

The master impedance measurement unit may be configured to generate a master clock signal. The master impedance measurement unit may further transmit the clock signal to each of the slave impedance measurement units for controlling the clocks 150 of all the impedance measurement units 120 and for ensuring that the clocks 150 are synchronized.

The clock 150 of each impedance measurement unit 120 may for instance control modulation of the input voltages in the I channel and Q channel, respectively, of the measurement circuit 130. This implies that the processing of input signals in acquiring impedance measurements is synchronized to avoid errors in the acquired impedance measurements.

Further, the master impedance measurement unit may be configured to control shifting of modes of the impedance measurement units 120. One impedance measurement unit 120 at a time will be set to the stimulation mode and other impedance measurement units 120 may be set to the measurement mode or the calibration mode. Thus, the control of shifting of modes may ensure that each impedance measurement unit 120 is set in the correct mode fitting with the modes of the other impedance measurement units 120.

The master impedance measurement unit may be configured to communicate a control signal for shifting the mode of slave impedance measurement unit via a control input interface 152. The control input interface 152 may comprise a connection to the master impedance measurement unit for receiving a control signal via a wired connection. The control signal from the master impedance measurement unit may be a signal initiating that the slave impedance measurement unit is to shift to a next mode. Thus, the control signal may be common to all slave impedance measurement units, since the control signal need not specify which mode each impedance measurement unit 120 is to assume, but rather may define a timing of when a shift is to be made.

Each impedance measurement unit 120 may comprise a sequencer unit 154. The sequencer unit 154 may store a sequence of modes such that each impedance measurement unit 120 may keep track of which mode to assume upon receiving the control signal from the master impedance measurement unit. On set-up of the system 100, each impedance measurement unit 120 may be provided with a sequence of modes to be used. Each time the system 100 is changed, e.g. by adding or removing impedance measurement units 120, the sequence of modes of all sequencer units 154 may need to be updated. For instance, when the number of impedance measurement units 120 is changed, a number of steps within a cycle defined by the sequence of modes is changed.

The impedance measurement units 120 may communicate with a processing unit, e.g. an external unit, for providing impedance measurement results. As mentioned above, the impedance measurement units 120 may form digital representations of the measured voltages before communicating results to the external unit. Thus, each impedance measurement unit 120 may comprise a digital communication interface 156.

The communication with the external unit may be provided through various communication protocols, such as serial peripheral interface (SPI), universal asynchronous receiver-transmitter (UART), or inter-integrated circuit (I2C).

According to an embodiment, all impedance measurement units 120 may be configured to share a wire for communication. This implies that the number of wires may be substantially reduced and that the complexity of the system 100 is reduced. Using I2C protocol, sharing of a wire for communication is supported, but there may be limitations in speed of communication. According to an alternative, a modified SPI protocol may be used. In the SPI protocol, separate chip select lines are used between a master and each slave. However, with the modified SPI protocol, chip select lines may be avoided by providing an encoding/decoding message on a single wire for selecting a chip. According to another alternative, a modified UART protocol may be used. The modified UART protocol may allow multiple transmitters on a single wire by adding an identifier section in a preamble of the UART protocol. The identifier section may identify a particular impedance measurement unit 120 such that the identified impedance measurement unit 120 may then use wire for communicating measurement results.

Referring again to FIG. 1, an electrode 110 may be shared by two neighboring impedance measurement units 120. This implies that impedance measurements may be performed between each pair of neighboring electrodes 110 in the plurality of electrodes 110. This may be advantageous in ensuring that impedance information from the subject 102 may be acquired over an entire area defined by the plurality of electrodes 110, such that there are no "holes" in which no impedance information is acquired. Since an electrode 110 is shared by two neighboring impedance measurement units 120, setting one impedance measurement unit 120 in the stimulation mode may also affect neighboring impedance measurement units 120. When an impedance measurement unit 120 is in the stimulation mode, a current is driven through the electrodes 110 associated with the impedance measurement unit 120 by the current generator 122. The electrodes 110 through which a current is driven may not be suited for also performing an impedance measurement at the same time. Since an electrode 110 may be shared by neighboring impedance measurement unit 120, setting one of the impedance measurement units 120 in the stimulation mode implies that the neighboring impedance measurement unit 120 may not be suited for performing impedance measurements at that point in time.

When each impedance measurement unit 120 is associated with two electrodes 120, two neighboring impedance measurement units 120 on opposite sides of the impedance measurement unit 120 set in the stimulation mode may thus be affected.

Figure 3:
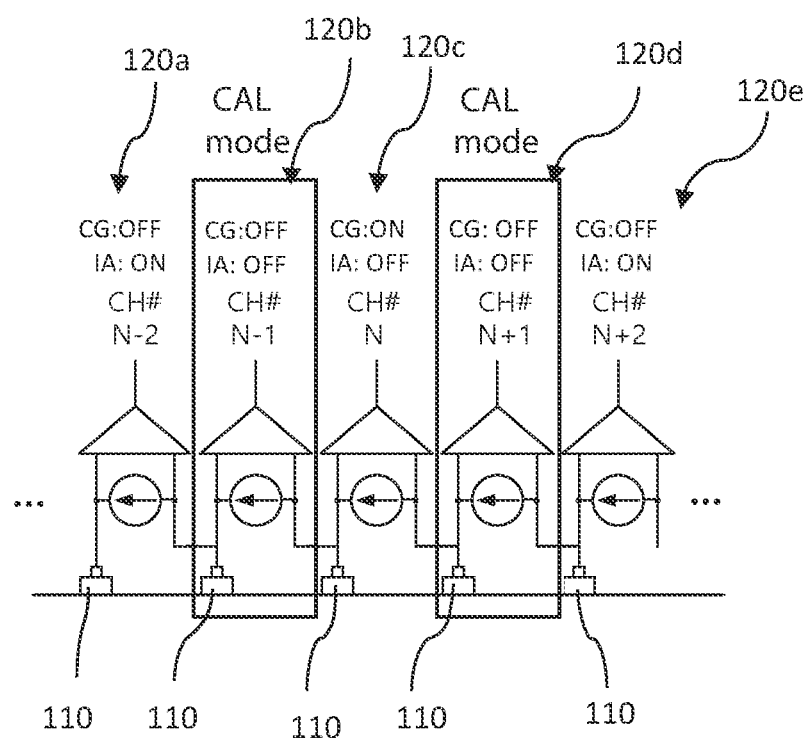
FIG. 3 is a schematic view of impedance measurement units being set in different modes of operation.

Referring now to FIG. 3, the fact that two neighboring impedance measurement units 120b, 120d on opposite sides of the impedance measurement unit 120c set in the stimulation mode are affected by the impedance measurement unit 120c being set in the stimulation mode is utilized by setting these neighboring impedance measurement units 120b, 120d in a calibration mode. Hence, at a point of time, when the impedance measurement units 120b, 120d are not suitable for being used in the measurement mode, the impedance measurement units 120b, 120d are instead set in the calibration mode. This implies that the impedance measurement units 120b, 120d may be set in the calibration mode during at least one of the plurality of impedance measurements being made. Thus, calibration of the impedance measurement units 120b, 120d may be performed during EIT measurements.

As illustrated in FIG. 3, impedance measurement units 120a, 120e may be set in the measurement mode for acquiring impedance measurements while impedance measurement unit 120c is in the stimulation mode. In fact, during the point in time when the impedance measurement unit 120c is set in the stimulation mode, a subset of impedance measurements may be acquired using each of the impedance measurement units 120a, 120e (and others not illustrated) which are not in the stimulation mode or in the calibration mode.

Further, since the impedance measurement units 120 are sequentially set in the stimulation mode, each impedance measurement unit 120 may at some point in time during acquisition of impedance measurements be neighboring to the impedance measurement unit 120 being set in the calibration mode.

Thanks to the impedance measurement units 120 being calibrated while the system 100 may be in use for acquiring impedance measurements, the impedance measurement units 120 may stay calibrated even if the system 100 is continuously used for a long period of time. This is especially suitable if the system 100 is used for monitoring of a subject 102, who may not be trained to perform calibration of the system 100. By having a system 100 which calibrates itself in the background without need of any interaction by a user/operator, the system 100 facilitates long-time use by subjects 102 without requiring any qualification of the subjects 102 for performing calibration.

Figure 4A:
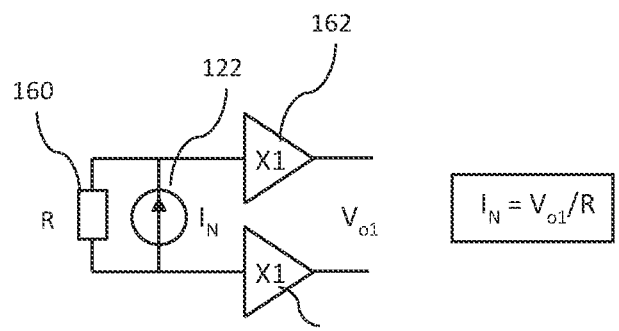
FIGS. 4a-b are schematic views illustrating calibration of the impedance measurement unit.
Figure 4B:
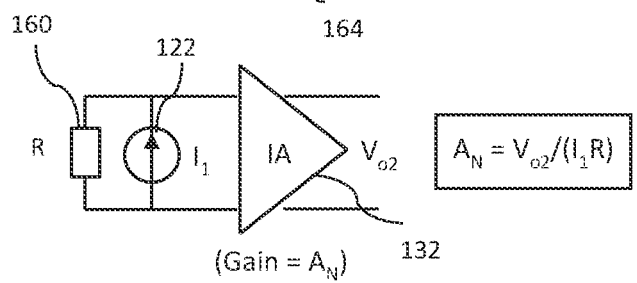

Referring now to FIGS. 4a-b, calibration operations will be further described. In FIG. 4a, calibration of the current generator 122 is illustrated, while in FIG. 4b, calibration of an amplifier 132, 134 is illustrated.

In the calibration mode, the impedance measurement unit 120 may be configured to calibrate a current generated by the current generator 122. The impedance measurement unit may further be configured to calibrate a gain of the amplifiers 132, 134 for each of the I channel and the Q channel of the measurement circuit 130.

The impedance measurement unit 120 may comprise a reference resistor 160, having a well-known resistance R. The reference resistor 160 may be arranged in the impedance measurement unit 120 for selectively being connected to the current generator 122 in the calibration mode, such that the current generated by the current generator 122 is driven through the reference resistor 160.

As illustrated in FIG. 4a, in calibration of the current generator 122, nodes on opposite sides of the current generator 122 may be connected to unity gain buffers 162, 164.

An amplitude of the current generated by the current generator may be determined by measuring a voltage between the nodes on opposite sides of the current generator 122 while the current generator 122 generates a current through the reference resistor 160 having a well-known resistance R. Thanks to connecting each node to a unity gain buffer 162, 164, connection of the nodes to an ADC 136 for obtaining a digital measurement of the voltage between the nodes is facilitated.

The ADC 136 used for reading an amplified measurement voltage in the measurement mode may be thus re-used in reading a voltage $V_{o1}$ for calibration of the current generator 122. Thus, as illustrated in FIG. 2, the amplifier 132 may be disconnected from the ADC 136 in the calibration mode, when calibrating the current generator 122, such that the nodes on opposite sides of the current generator 122 are instead connected to unity gain buffers 162, 164 which are further connected to the ADC 136.

As shown in FIG. 4a, the current IN generated by the current generator 122 may be determined as $I_N = V_{o1}/R$.

Calibration of the current generated by the current generator 122 may comprise determining an amplitude of the current generated by the current generator 122 and storing the measured amplitude so as to enable the stored measured amplitude to be used as compensation when forming an EIT image. The measured amplitude may be transmitted to the processing unit such that the processing unit may store compensation values for the current generators 122 of all impedance measurement units 120.

The calibration of the current generator 122 may use only one channel, as indicated above. The current generator 122 may thus be connected in the I channel to unity gain buffers 162, 164 for providing a signal to the ADC 136. However, it should be realized that the calibration of the current generator 122 may alternatively use both the I channel and the Q channel, wherein nodes on opposite sides of the current generator 122 may be connected to unity gain buffers instead of the amplifier 134, as illustrated in FIG. 2.

Using both channels may provide a more reliable calibration of the current generator 122. If the calibration load is purely resistive, the Q channel will give virtually zero output. However, if there is any effect of parasitic capacitances, the Q channel may contribute to a reliable calibration.

As illustrated in FIG. 4b, in calibration of the amplifier 132, 134, nodes on opposite sides of the current generator 122 may be connected to the amplifier 132, 134 while the current generator 122 drives a current through the reference resistor 160. In FIG. 4b, calibration of the amplifier 132 of the I channel is illustrated. However, it should be realized that calibration of the amplifier 134 of the Q channel may be performed in corresponding manner.

In this calibration, the current generated by the current generator 122 may be assumed to be known, represented here as $I_1$. The current may be known by the calibration of the current generator 122 being performed before the calibration of the amplifier 132. Alternatively, calibration of the current generator 122 and calibration of the amplifier(s) 132, 134 need not be performed each time the impedance measurement unit 120 is set in the calibration mode. Rather, the current generator 122 may be calibrated during a first time when the impedance measurement unit 120 is in the calibration mode and the amplifier(s) 132, 134 may be calibrated during a second time when the impedance measurement unit 120 is in the calibration mode. Thus, it may be assumed that the current generated by the current generator 122 has not changed or changed insignificantly between two subsequent times of the impedance measurement unit 120 being in the calibration mode.

Thus, the voltage input to the amplifier 132 is known and corresponds to $I_1*R$. The ADC 136 may again be used in reading a voltage $V_{o2}$ for calibration of the amplifier 132. Thus, the measured voltage $V_{o2}$ may be compared to the input voltage for determining the gain of the amplifier 132.

As shown in FIG. 4a, the gain $A_N$ of the amplifier 132 may be determined as $A_N=V_{o2}/(I_1*R)$.

Calibration of the gain provided by the amplifiers 132, 134 may comprise measuring a gain of each amplifier 132, 134 and storing the measured gain so as to enable the stored measured gain to be used as compensation when forming an EIT image. The measured gain may be transmitted to the processing unit such that the processing unit may store compensation values for the amplifiers 132, 134 of all impedance measurement units 120.

Figure 5:
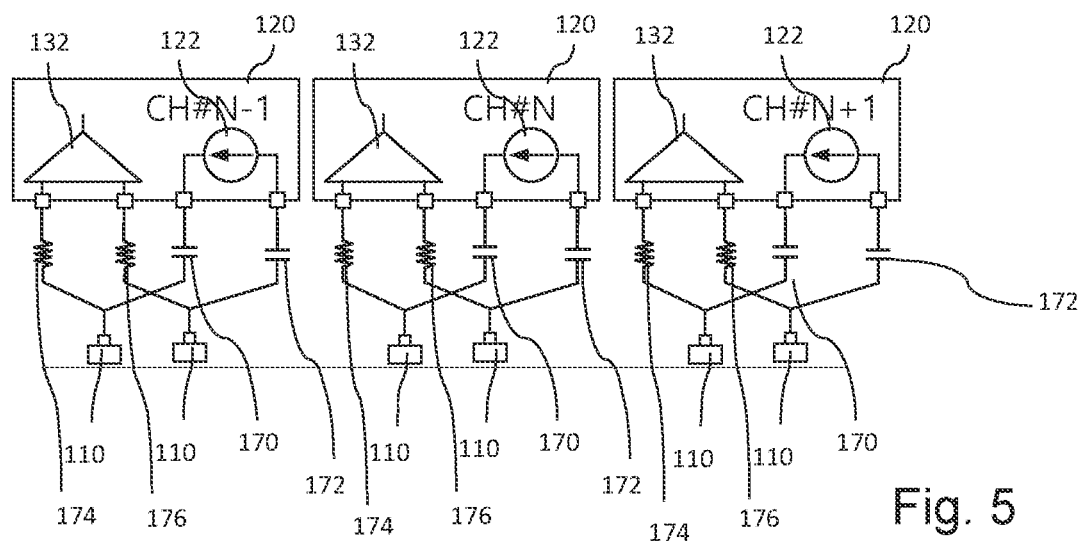
FIG. 5 is a schematic view illustrating a safety circuit between impedance measurement units and electrodes.

Referring now to FIG. 5, the system 100 may provide at least one safety circuit connecting impedance measurement units 120 to the electrodes 110. The at least one safety circuit may prevent transient current spikes from causing harm to the subject 102.

As illustrated in FIG. 5, the safety circuit may be configured to provide an interface between the impedance measurement unit 120 and the electrodes 110. Components of the safety circuit may thus be arranged in the impedance measurement unit 120 to provide a desired interface to the electrodes 110.

It should be noted that the electrodes 110 are illustrated in FIG. 5 as being associated with specific impedance measurement units 120 and that electrodes 110 are not shown to be shared by two impedance measurement units 120. This is mainly done in order to more clearly show the connections to the impedance measurement units 120 and it should be understood that the interfaces between the impedance measurement unit 120 and the electrodes 110 may be configured in the same manner even if electrodes 110 are shared by neighboring impedance measurement units 120.

According to the embodiment illustrated in FIG. 5, each impedance measurement unit 120 comprises DC blocking capacitors 170, 172 in connections between the current generator 122 and the electrodes 110 associated with the impedance measurement unit 120. Further, each impedance measurement unit 120 comprises resistors 174, 176 in connections between the amplifiers 132, 134 (here, only amplifier 132 is illustrated) and the electrodes 110 associated with the impedance measurement unit 120.

This implies that transient current spikes may be prevented from reaching or at least reduced before reaching the subject 102. This is a simple circuitry while providing safety to the subject 102 on which EIT measurements are performed.

Figure 6:
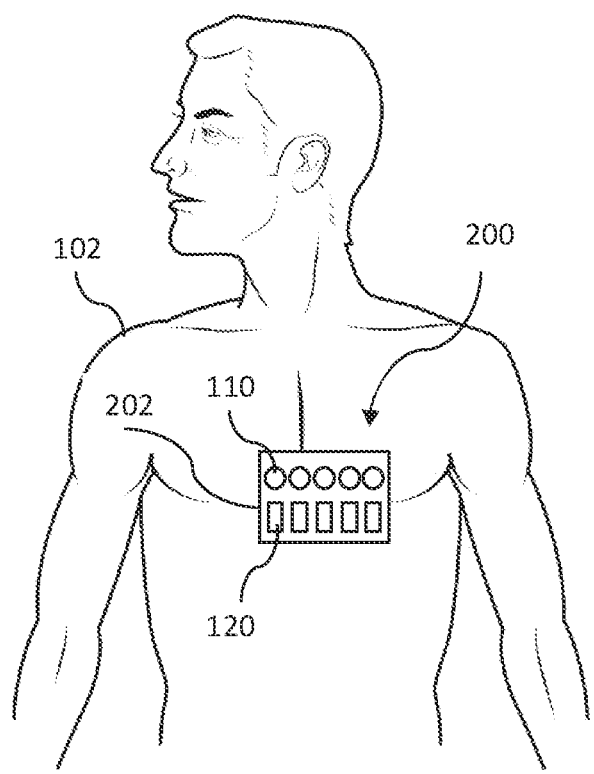
FIG. 6 is a schematic view of an electrical impedance tomography apparatus according to an embodiment.

Referring now to FIG. 6, an EIT apparatus 200 is described. The EIT apparatus may be provided in a carrier 202, which is configured to be worn by a subject 102. The system 100 described above may be arranged on the carrier 202. Although it is described above that the system 100 may be versatile such that it may be separately defined, e.g. in terms of number of impedance measurement units 120, in relation to the application in which the system 100 is used, it should be realized that the system 100 may be provided in a fixed configuration on the carrier 202. The carrier 202 may further define positions of electrodes 100 in relation to the subject 102, for arranging electrodes 100 in a desired relation to the subject 102.

The EIT apparatus 200 may thus be manufactured with a set-up of the system 100 fit to the use of the EIT apparatus 200 for monitoring bioimpedance of a subject 102. However, it should be realized that in another embodiment, a general carrier 202 may be used which may define multiple potential positions of electrodes 110 and corresponding arrangements of impedance measurement units 120 on the carrier 202, but the carrier 202 may be configured for setting different relations to the subject 102 for monitoring different body parts and, thus, depending on the use of the EIT apparatus 200 different number of positions of electrodes 110 may be filled. Thus, the EIT apparatus 200 may even be adapted by an end-user between different sessions of measurements relating to different body parts being monitored. For instance, the carrier 202 may be provided in a form of a belt or band that may be arranged around a body part and wherein a size of the belt or band may be adjusted in dependence of what body part the carrier 202 is to be arranged around. The carrier 202 may thus be selectively arranged around a torso, around a leg or around an arm of the subject 102.

As shown in FIG. 6, the carrier 202 may alternatively be a patch which is configured to be attached to the subject 102. The arrangement of the carrier 202 in relation to the subject 102 may ensure that electrodes 110 are arranged in good contact with the subject 102 for facilitating performing of the EIT measurements.

Figure 7:
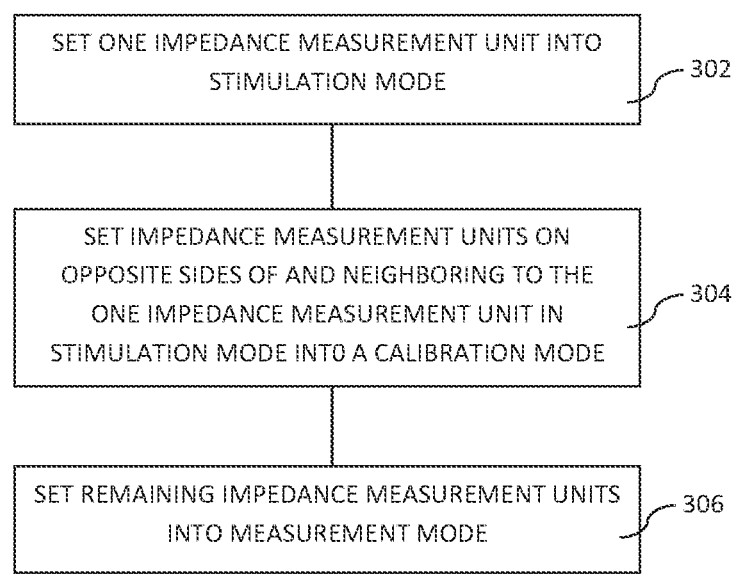
FIG. 7 is a flowchart of a method according to an embodiment.

Referring now to FIG. 7, a method for performing EIT measurements on a subject 102 will be described. The method is performed using the system 100 described above comprising a plurality of electrodes 110 and a plurality of impedance measurement units 120, wherein neighboring impedance measurement units 120 share an electrode 110.

The method comprises setting 302 one impedance measurement unit 120c into a stimulation mode for providing a stimulation current into the subject 102 between the electrodes 110 associated with the one impedance measurement unit 120c.

The method further comprises setting 304 impedance measurement units 120b, 120d on opposite sides of and neighboring to the one impedance measurement unit 120c being set in the stimulation mode into a calibration mode for calibration of the impedance measurement unit 120b, 120d.

The method further comprises setting 306 impedance measurement units 120a, 120e not being in the stimulation mode or the calibration mode into a measurement mode for measuring a voltage between the electrodes 110 associated with the impedance measurement unit 120.

This implies that impedance measurement units 120b, 120d may be calibrated while other impedance measurement units 120a, 120e are performing impedance measurements. Thus, the system 100 may be calibrated during use and impedance measurement units 120b, 120d, which may anyway not be suited for performing impedance measurements at a specific point in time may utilize such point in time for calibration.

Further, the method may comprise switching the impedance measurement unit 120 being set in the stimulation mode and, hence, also switch impedance measurement units 120 being set in the calibration mode and in the measurement mode. The switching of modes may continue until all impedance measurement units 120 have been set in the stimulation mode such that impedance measurements have been acquired for forming an EIT image. During acquisition of the impedance measurements, all impedance measurement units 120 may also have been set in the calibration mode such that all impedance measurement units 120 are calibrated during one period of acquiring impedance measurements for forming one EIT image.

Although two impedance measurement units 120 are shown as being set in the measurement mode, it should be realized that many more electrodes 110 and impedance measurement units 120 may be used, such as more than 10, more than 50, or more than 100 electrodes may be used. In such case, at a single point in time, a large amount of impedance measurements may be performed such that a large amount of information for forming the EIT image may be acquired.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A system for electrical impedance tomography of an object, said system comprising:
   a plurality of electrodes configured to be attached to the object;
   a plurality of impedance measurement units, wherein each impedance measurement unit is associated with two or more electrodes of the plurality of electrodes, and wherein each impedance measurement unit comprises a current generator for generating a stimulation current between the electrodes associated with the impedance measurement unit and an amplifier for amplifying a measurement voltage between the electrodes associated with the impedance measurement unit;
   wherein the system is configured to perform a plurality of impedance measurements, wherein, for each impedance measurement, one impedance measurement unit among the plurality of impedance measurement units is set in a stimulation mode for providing a stimulation current into the object between the electrodes associated with the one impedance measurement unit, and wherein the impedance measurement unit being set in the stimulation mode is switched among the plurality of impedance measurement units between different measurements in the plurality of impedance measurements, and
   wherein each impedance measurement unit is configured to be set in a calibration mode during at least one of the plurality of impedance measurements for calibration of the impedance measurement unit during electrical impedance tomography measurements.

2. The system according to claim 1, wherein each impedance measurement unit is configured to be set in the stimulation mode during at least one impedance measurement of the plurality of impedance measurements.

3. The system according to claim 1, wherein, in the calibration mode, the impedance measurement unit is configured to calibrate a current generated by the current generator of the impedance measurement unit.

4. The system according to claim 3, wherein the impedance measurement unit comprises unity gain buffers configured to be connected to nodes on opposite sides of the current generator in calibration measurements for calibrating the current generated by the current generator.

5. The system according to claim 1, wherein, in the calibration mode, the impedance measurement unit is configured to calibrate a gain of the amplifier.

6. The system according to claim 1, wherein each impedance measurement unit comprises a reference resistor, which is configured to be connected to the current generator in the calibration mode for calibration of the impedance measurement unit.

7. The system according to claim 1, wherein each impedance measurement unit is associated with two neighboring electrodes in the plurality of electrodes, and wherein an electrode is shared by two neighboring impedance measurement units in the plurality of impedance measurement units.

8. The system according to claim 7, wherein, for a subset of impedance measurements in the plurality of impedance measurements, the subset being acquired at a single point in time, two impedance measurement units being arranged on opposite sides of and neighboring to the one impedance measurement unit being set in the stimulation mode are configured to be set in the calibration mode.

9. The system according to claim 1, wherein, for a subset of impedance measurements in the plurality of impedance measurements, the subset being acquired at a single point in time, each impedance measurement unit not being in the stimulation mode or the calibration mode is set in a measurement mode for measuring a voltage between the electrodes associated with the impedance measurement unit.

10. The system according to claim 1, wherein the system is configured to set one of the impedance measurement units in the plurality of impedance measurement units as a master impedance measurement units and remaining impedance measurement units as slave impedance measurement units, wherein the master impedance measurement unit is configured to communicate with the slave impedance measurement units for controlling operation of the slave impedance measurement units.

11. The system according to claim 10, wherein the master impedance measurement unit is configured to generate a master clock signal and to transmit the clock signal to the slave impedance measurement units for synchronizing clocks of the plurality of impedance measurement units.

12. An electrical impedance tomography apparatus comprising the system according to claim 1, wherein the apparatus is configured to be worn by a subject and wherein the apparatus is configured to continuously monitor bioimpedance of the subject while the apparatus is worn.

13. A method for electrical impedance tomography of an object by a system comprising a plurality of electrodes and a plurality of impedance measurement units wherein each impedance measurement unit is associated with two electrodes of the plurality of electrodes, said method comprising for performing an impedance measurement:

setting one impedance measurement unit into a stimulation mode for providing a stimulation current into the object between the electrodes associated with the one impedance measurement unit;

setting impedance measurement units on opposite sides of and neighboring to the one impedance measurement unit being set in the stimulation mode into a calibration mode for calibration of the impedance measurement unit; and setting impedance measurement units not being in the stimulation mode or the calibration mode into a measurement mode for measuring a voltage between the electrodes associated with the impedance measurement unit.

* * * * *